United States Patent
Raman et al.

(10) Patent No.: US 11,674,419 B1
(45) Date of Patent: Jun. 13, 2023

(54) ENGINE SYSTEM WITH CATALYTIC REACTOR

(71) Applicant: SAUDI ARABIAN OIL COMPANY, Dhahran (SA)

(72) Inventors: Vallinayagam Raman, Dhahran (SA); Seung-Hak Choi, Dhahran (SA); Junseok Chang, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 0 days.

(21) Appl. No.: 17/456,497

(22) Filed: Nov. 24, 2021

(51) Int. Cl.
 *F01N 3/20* (2006.01)
 *F01N 3/035* (2006.01)

(52) U.S. Cl.
 CPC ............ *F01N 3/035* (2013.01); *F01N 3/20* (2013.01); *F01N 2240/30* (2013.01); *F01N 2570/10* (2013.01); *F01N 2570/22* (2013.01); *F01N 2590/02* (2013.01); *F01N 2610/04* (2013.01)

(58) Field of Classification Search
 CPC .... F01N 3/20; F01N 2240/30; F01N 2610/04; F01N 2570/10; F01N 2570/22; F01N 2590/02
 See application file for complete search history.

(56) References Cited

U.S. PATENT DOCUMENTS

| | | | |
|---|---|---|---|
| 4,476,817 A * | 10/1984 | Lindberg | F02M 25/00 123/25 J |
| 7,089,888 B2 | 8/2006 | Mirji | |
| 8,984,864 B2 | 3/2015 | Cockle et al. | |
| 9,334,204 B1 | 5/2016 | Radaelli et al. | |
| 9,617,490 B2 | 4/2017 | Weiss et al. | |
| 10,815,123 B2 | 10/2020 | Northrop | |
| 2008/0293980 A1 | 11/2008 | Kiesslich et al. | |
| 2012/0028142 A1 | 2/2012 | Whyatt et al. | |
| 2012/0291424 A1 | 11/2012 | Inuzuka et al. | |
| 2013/0298862 A1 | 11/2013 | Penman | |
| 2016/0290288 A1 * | 10/2016 | LaPointe | F02M 26/06 |
| 2016/0319779 A1 * | 11/2016 | LaPointe | F01N 3/101 |
| 2017/0348659 A1 | 12/2017 | Northrop | |
| 2018/0094612 A1 | 4/2018 | Henry | |
| 2020/0217278 A1 * | 7/2020 | Henry | F02M 26/05 |

FOREIGN PATENT DOCUMENTS

| | | |
|---|---|---|
| EP | 1269006 A1 | 1/2003 |
| FR | 2993933 A1 | 1/2014 |
| KR | 101589243 B1 | 1/2016 |

OTHER PUBLICATIONS

International Search Report and the Written Opinion of the International Searching Authority dated Mar. 13, 2023 in corresponding International (PCT) Application No. PCT/US2022/050891.

* cited by examiner

*Primary Examiner* — Carl C Staubach
*Assistant Examiner* — Diem T Tran
(74) *Attorney, Agent, or Firm* — Osha Bergman Watanabe & Burton LLP

(57) ABSTRACT

An engine system includes an engine configured to combust liquid natural gas and generate an exhaust gas comprising methane; a catalytic reactor coupled downstream of the engine and configured to convert methane into a product through one or more of oxidative coupling of methane (OCM) reaction and steam methane reforming (SMR) reaction; and a recirculation loop configured to recirculate at least a part of the product back to the engine.

19 Claims, 7 Drawing Sheets

ENGINE SYSTEM WITH CATALYTIC REACTOR

BACKGROUND

Conventional fuels used in marine engines may include heavy fuel oil (HFO), very-low sulfur fuel oil (VLSFO), and marine gas oil (MGO). However, to reduce greenhouse gas emission and air pollutant emission, liquid natural gas (LNG) may be used as an alternative. LNG comprises little sulfur, which leads to less sulfur oxide ($SO_x$) emissions after combustion. Further, marine engines fueled by LNG produces less carbon emission per unit energy. When LNG is used at lean burn conditions in a spark ignited (SI) or dual-fuel combustion processes, emission of nitrogen oxide ($NO_x$) may also be reduced. As such, the use of LNG in marine engines is feasible with air quality and climate change concerns.

While less carbon dioxide ($CO_2$) is produced when using LNG as fuel in marine engines, "methane slip" may occur and contribute to greenhouse gas emissions. Methane slip refers to uncombusted methane due to incomplete combustion in the engine. Fuel trapped in the crevice of the piston escaping the engine and exiting with the exhaust stream also contributes to methane slip. Methane ($CH_4$), which is the main component of LNG, is a greenhouse gas that traps much more heat when compared to an equivalent amount of carbon dioxide. Although post-oxidation methods may be used to oxidize unburnt methane, this process may contribute to increased carbon dioxide emissions.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

One or more aspects of the disclosure relate to an engine system comprising an engine configured to combust liquid natural gas and generate an exhaust gas comprising methane; a catalytic reactor configured to convert methane into a product through one or more of oxidative coupling of methane (OCM) reaction and steam methane reforming (SMR) reaction; and a recirculation loop configured to recirculate at least a part of the product back to the engine.

In one aspect, the catalytic reactor is configured to convert methane through the OCM reaction and comprises an oxygen permeable membrane. The recirculation loop is configured to recirculate ethylene to the engine.

In another aspect, the catalytic reactor is configured to convert methane through the OCM reaction. The engine system further comprises a treatment device coupled to the recirculation loop, configured to remove carbon dioxide, water, or both, from the product. The recirculation loop is configured to recirculate the product to the engine after removal of carbon dioxide, water, or both.

In yet another aspect, the catalytic reactor is configured to convert methane through the SMR reaction and comprises a hydrogen permeable membrane. The recirculation loop is configured to recirculate hydrogen that permeates through the hydrogen permeable membrane to the engine.

In yet another aspect, the catalytic reactor is configured to convert methane through the SMR reaction. The engine system further comprises a treatment device coupled to the recirculation loop, configured to remove carbon dioxide, water, or both, from the product. The recirculation loop is configured to recirculate the product to the engine after removal of carbon dioxide, water, or both.

In yet another aspect, the catalytic reactor is configured to convert methane through the OCM reaction and the SMR reaction. The catalytic reactor comprises a hydrogen permeable membrane. The recirculation loop recirculates hydrogen that permeates the hydrogen permeable membrane to the engine.

In yet another aspect, the catalytic reactor converts methane through the OCM reaction and the SMR reaction. The engine system further comprises a treatment device coupled to the recirculation loop, configured to remove carbon dioxide, water, or both, from the product. The recirculation loop recirculates the product, after removal of carbon dioxide, water, or both, water, to the engine.

Another one or more aspects of the disclosure relate to a method comprising: operating an engine system such that a fuel comprising liquid natural gas in an engine; directing an exhaust gas comprising methane from the engine to a catalytic reactor; converting methane to a product through one or more of oxidative coupling of methane (OCM) reaction and steam methane reforming (SMR) reaction; and recirculating at least a part of the product to the engine.

In one aspect, the method comprises converting methane to the product through the OCM reaction; supplying oxygen to the catalytic reactor through an oxygen permeable membrane; and recirculating ethylene in the product to the engine.

In another aspect, the method comprises converting methane to the product through the OCM reaction; removing carbon dioxide, water, or both, from the product; and recirculating the product, after the removing carbon dioxide and/or water, to the engine.

In yet another aspect, the method comprises converting methane to the product through the SMR reaction; obtaining hydrogen from the product using a hydrogen permeable membrane; and recirculating hydrogen that permeates the hydrogen permeable membrane to the engine.

In yet another aspect, the method comprises converting methane to the product through the SMR reaction; removing carbon dioxide, water, or both, from the product; and recirculating the product, after the removing carbon dioxide, water, or both, to the engine.

In yet another aspect, the method comprises converting methane to the product through the OCM and the SMR reaction; obtaining hydrogen from the product using a hydrogen permeable membrane; and recirculating hydrogen that permeates the hydrogen permeable membrane to the engine.

In yet another aspect, the method comprises converting methane to the product through the OCM and the SMR reaction; removing carbon dioxide, water, or both, from the product; and recirculating the product, after the removing carbon dioxide, water, or both, to the engine.

Other aspects and advantages of the claimed subject matter will be apparent from the following Detailed Description and the appended Claims.

DETAILED DESCRIPTION

Figure 1A:
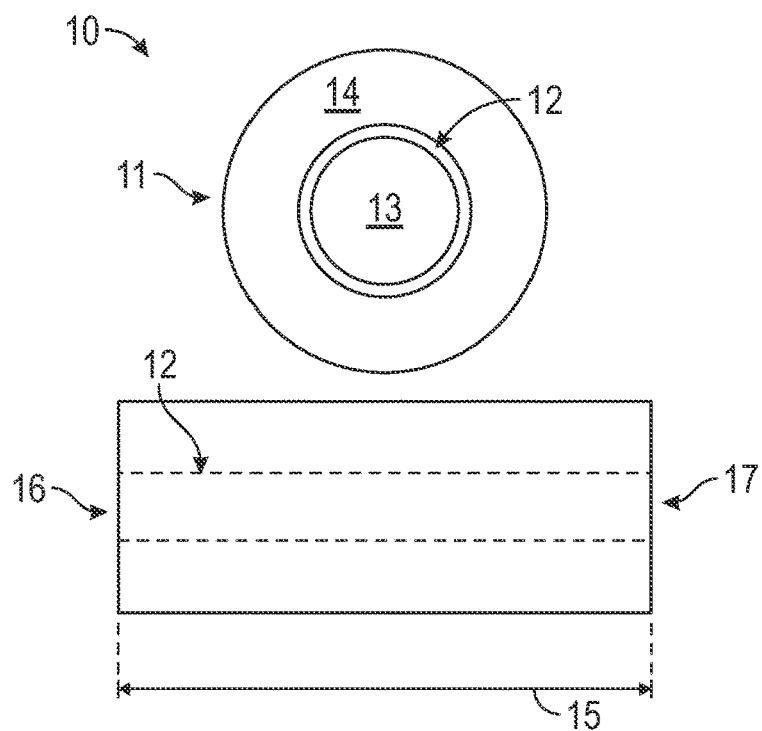
FIG. 1A is an end-view and a side view of a first membrane-based reactor according to one or more embodiments.

In the following, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

One or more embodiments of the present disclosure relate to a marine engine system comprising an engine using LNG as fuel and a catalytic reactor to break down uncombusted methane, that is, methane slip, into useful products. Preventing uncontrolled emissions reduces contributions of greenhouse gases to the environment while using much cleaner-burning fuel. The engine may generate an exhaust gas comprising uncombusted methane. The exhaust may then be directed to the catalytic reactor for facilitating reactions with methane. The engine exhaust gas may have waste heat sufficient to activate catalysts and accelerate reactions in the catalytic reactor. The products from the reactions may be in part recirculated back into the engine. In one or more embodiments, at least one gas from the reactions is recirculated back to the engine through an intake of the engine or exhaust gas recirculation (EGR). In one or more embodiments, the catalytic reactor is a membrane-based reactor that utilizes exhaust heat from the engine to facilitate the reactions with unburnt methane.

The engine configuration according to one or more embodiments may be a compression ignition engine or a spark ignition engine. In compression ignition engines, LNG as fuel is introduced into the combustion chamber where the air is already present in a compressed form. The elevated temperature and pressure within the chamber cause the fuel to auto-ignite. "Elevated" means greater than atmospheric conditions. The combustion process follows via mixing of air-fuel mixture through diffusion. In one or more embodiments, the engine configuration may be a dual fuel compression ignition engine operating under either a high-pressure dual fuel (HPDF) or a low-pressure dual fuel (LPDF) condition. Both dual-fuel technologies use lean fuel mixtures, that is, a fuel mixture with excess air (high air-to-fuel ratio). A small amount of diesel fuel is utilized as a pilot igniter.

In the spark ignition (SI) engine, the air-fuel mixture is introduced into a cylindrical combustion chamber for ignition via spark plug. As the resulting flame front propagates through the combustion chamber from the initial ignition point, the temperature continues to rise, which in turn leads to high peak combustion temperatures. In one or more embodiments, the spark ignition engine may be a stoichiometric spark ignited engine with an air-to-fuel ratio of 14.64:1. In one or more embodiments, the spark ignition engine may be a lean burn spark ignited (LBSI) engine having an air-to-fuel ratio of up to about 65:1. A lean-burn engine may emit far less hydrocarbons due to the excess amount of oxygen (via the air) being used. High air-to-fuel ratio may also reduce losses caused by other engine power management systems, such as throttling losses.

According to one or more embodiments, the catalytic reactor may perform reactions utilizing oxidative coupling of methane (OCM) to convert methane into useful products. OCM processes convert methane into ethylene, presented by Formula 1:

$$2CH_4 + O_2 = C_2H_4 + 2H_2O \qquad \text{(Formula 1)}$$

The oxidative coupling of methane reaction is exothermic ($\Delta H_{OCM} = -280$ kJ/mol) and occurs at elevated temperatures. During reaction, methane is activated heterogeneously on a surface of a catalyst, forming methyl free radicals. Two methyl free radicals couple in the gas phase to form ethane ($C_2H_6$). At the elevated conditions, the ethane subsequently undergoes dehydrogenation (also known as "cracking") and forms the olefin ethylene ($C_2H_4$). The yield of the desired $C_2$ hydrocarbons may be reduced by non-selective reactions (for example, selective oxidation reactions) of methyl radicals with the catalyst surface and oxygen in the gas phase, which produce (undesirable) combustion byproducts, including carbon monoxide (CO) and carbon dioxide ($CO_2$). OCM catalyst may be used to increase the yield of ethylene, improve the selectivity of conversion, and reduce the operating temperature of the OCM system. In one or more embodiments, the ethylene generated from the OCM reaction may be recirculated back to the engine, which may increase combustion efficiency. In one or more embodiments, the ethylene may be separated and captured from the exhaust stream for conversion into useful chemical products beyond the scope of this application.

According to one or more embodiments, the catalytic reactor may perform reactions utilizing SMR to convert methane into useful products. SMR is a reaction of methane with water, converting methane into a syngas, that is, hydrogen and carbon monoxide, presented by Formula 2:

$$CH_4 + H_2O = CO + 3H_2 \qquad \text{(Formula 2)}$$

The SMR reaction is endothermic ($\Delta H_{SMR} = +206$ kJ/mol). A SMR catalyst may be used for the SMR reaction. Further, waste heat brought by the exhaust gas may thermally contribute to the SMR reaction. The produced hydrogen may be used as a supplementary fuel to improve the efficiency of the engine or may be separated and recovered for other uses outside the scope of this application.

According to one or more embodiments, the catalytic reactor may be a membrane-based reactor comprising a membrane. Compared to conventional reactors, membrane-based reactors increase the yield of products (ethylene from OCM; hydrogen from SMR). Further, the membrane-based reactors may have an increased conversion efficiency by coupling selectivity with catalytic activity. In one or more embodiments, the membrane may be an oxygen permeable membrane or a hydrogen permeable membrane based on polymer, carbon, metal, or ceramic materials of construction. The membrane may be dense or porous. In one or more embodiments, the membrane may be based on solution-

diffusion mechanism. In one or more embodiments, the membrane may comprise palladium (Pd), silver (Ag), yttrium (Y), copper (Cu), or alloys thereof. In one or more embodiments, the membrane may comprise silica, alumina, zirconia, titania, or zeolite molecular sieve. In one or more embodiments, the membrane may be based on perovskite or yttria-stabilized zirconia (YSZ), optionally doped to increase conductivity or number of oxygen vacancies. In one or more embodiments, the membrane may comprise microporous carbon, for example, a carbon molecular sieve.

The catalytic reactor may be used to perform OCM reaction using a OCM catalyst to generate ethylene with a first yield of at least 60% based on methane conversion. In one or more embodiments, the first yield may be 70% or more, such as 75% or more, such as 80% or more, or such as 85% or more based on methane conversion.

In one or more embodiments, oxygen produced by conventional methods, such as pressure swing adsorption (PSA) process, may be directly fed to the OCM reaction. In one or more embodiments, air may be fed to the OCM reaction and the catalytic reactor is a membrane-based reactor. The membrane-based reactor may have an oxygen permeable membrane that allows selective permeation of oxygen. Air feed containing oxygen may be supplied to the feed side of the membrane. Oxygen is selectively separated from the air feed utilizing the membrane and is received along the length of the reactor to favor the reactions on the permeate side of the membrane. Additional oxygen may reduce undesired side-reactions resulting in carbon monoxide and carbon dioxide formation. At least one or more gas from OCM reaction may be recirculated back to the engine.

In one or more embodiments, ethylene may be recirculated directly to an intake of the engine. In one or more embodiments, one or more of unreacted methane, ethylene, carbon monoxide, and other species from the OCM reaction may be recirculated back via reformed exhaust gas recirculation (EGR).

In one or more embodiments, carbon dioxide, water, or both, may be removed from the products of the reaction through a treatment device coupled to the recirculation loop. The treatment device may comprise a treatment membrane comprising, for example, zeolite, silica, or carbon. The treatment device may further comprise a vacuum pump to generate a driving force to facilitate permeation of carbon dioxide, water, or both. After removal of carbon dioxide, water, or both, the retentate comprising components from the OCM reaction may be recirculated back to the engine, for example, through the EGR.

In one or more embodiments, a temperature control device may be used to control a temperature of the reactor, for example, to provide heating or cooling, to raise or reduce the temperature to a desired degree to induce reaction.

The catalytic reactor may be used to perform SMR reaction using a second catalyst to generate syngas (CO and $H_2$) with a second yield. The exhaust gas containing methane may be supplied into the reactor with water (for example, in form of steam). The SMR reaction may occur at the catalyst surface to generate a syngas. The second yield may depend on catalyst and conditions used in the SMR reaction.

Despite a second yield that varies, high purity hydrogen may be obtained through a membrane. For example, the catalytic reactor may be a membrane-based reactor having a hydrogen permeable membrane that allows selective permeation of hydrogen. While hydrogen permeates through the membrane, carbon monoxide is rejected and remains in the retentate. In one or more embodiments, the permeated high purity hydrogen may be recirculated back into the intake of the engine to increase flame speed and improve combustion. All other gases may be discharged outside the marine engine system. When high purity hydrogen is recirculated through an intake of the engine, combustion efficiency of the engine may be greatly improved.

In one or more embodiments, one or more of hydrogen, carbon monoxide, and unreacted methane may be recirculated back to the engine. Alternatively, hydrogen and carbon monoxide may be stored in a separate tank. Gases that are not recirculated or stored may be discharged outside the marine engine system.

In one or more embodiments, carbon dioxide, water, or both, may be removed from the products of the reaction through a treatment device coupled to the recirculation loop. The treatment device may comprise a treatment membrane comprising, for example, zeolite, silica, or carbon. The treatment device may further comprise a vacuum pump to generate a driving force to facilitate permeation of carbon dioxide, water, or both. After removal of carbon dioxide, water, or both, the remaining retentate components (for example, carbon monoxide, $C_2$ hydrocarbon, unreacted methane, air) from the SMR reaction may be recirculated back to the engine, optionally combined with high purity hydrogen.

In one or more embodiments, a temperature control device may be used to control a temperature of the reactor, for example, to provide heat or cooling, to either raise or reduce the temperature to a desired degree to induce reaction.

The catalytic reactor may be used to perform both OCM and SMR reactions using a third catalyst, which may be a dual function catalyst or a combination of the first catalyst and the second catalyst, to generate both ethylene and syngas (CO and $H_2$). The third yield may be at least 60% based on methane conversion. In one or more embodiments, the third yield may be 70% or more, such as 80% or more, such as 85% or more, such as 90% or more, or such as 95% or more based on methane conversion. Each of the OCM and SMR reactions are as previously described. Water (for example, in form of steam) and air or oxygen may be supplied to the catalytic reactor. The catalytic reactor may comprise an oxygen permeable membrane.

In one or more embodiments, the catalytic reactor may be a membrane-based reactor having a hydrogen permeable membrane that allows selective permeation of hydrogen. The permeated high purity hydrogen may be recirculated back into an intake of the engine to increase flame speed and improve combustion.

In one or more embodiments, one or more of hydrogen, carbon monoxide, and unreacted methane may be recirculated back to the engine. Gases that are not recirculated or stored may be discharged outside the marine engine system.

In one or more embodiments, carbon dioxide, water, or both may be removed from the products of the reaction through a treatment device coupled to the recirculation loop. The treatment device may comprise a treatment membrane comprising, for example, zeolite, silica, or carbon. The treatment device may further comprise a vacuum pump to generate a driving force to facilitate permeation of carbon dioxide, water, or both. After removal of carbon dioxide, water, or both, all the retentate components (for example, carbon monoxide, $C_2$ hydrocarbon, unreacted methane, air) from the reactions may be recirculated back to the engine, optionally combined with high purity hydrogen.

In one or more embodiments, a temperature control device may be used to control a temperature of the reactor, for example, to provide heat or cooling, to either raise or reduce the temperature to a desired degree to induce reaction.

The catalytic reactor according to one or more embodiments may be any conventional reactor used for OCM, SMR, or both reactions. For example, the catalyst reactor may be a compact reactor comprising a combustion zone and a catalyst bed among a refractory-lined pressure shell. In one or more embodiments, the catalytic reactor may be a membrane-based reactor.

According to one or more embodiments, the catalytic reactor may be a membrane-based reactor having one or more chambers in any suitable configuration. For example, the membrane-based reactor may have a multi-tubular configuration formed by one or more concentric tubes. FIG. 1A is an end-view and a side view of a first membrane-based reactor according to one or more embodiments. The first membrane-based reactor 10 comprises a tubular exterior shell 11 and a tubular interior shell 12 concentrically positioned such that the tubular interior shell 12 is within the interior void formed by the exterior shell 11. Exterior shell 11 is not permeable to any of the fluids utilized in or created by membrane-based reactor 10. The concentric positioning of the tubular interior shell 12 within the tubular exterior shell 11 creates two void spaces along the length 15 (between first end 16 and second end 17 of membrane-based reactor 10) of the membrane-based reactor 10: an interior fluid conduit 13 and an annular fluid conduit 14. In one or more embodiments, a part or all of the tubular interior shell is formed by a membrane.

In one or more embodiments, the membrane of the membrane-based reactor selectively permits oxygen to permeate through the membrane. In one or more embodiments, the membrane of the membrane-based reactor selectively permits hydrogen to permeate through the membrane.

In one or more embodiments, a catalyst for the OCM reaction is located in the annular fluid conduit. In one or more embodiments, the catalyst is coated on an interior surface of the exterior shell. In one or more embodiments, the catalyst is coated on an exterior surface of the membrane. In one or more embodiments, the catalyst is located in the interior fluid conduit. In one or more embodiments, the catalyst is coated on an interior surface of the membrane. In one or more embodiments, the catalyst is located in pores of the membrane.

In one or more embodiments, a catalyst for the SMR reaction is located in the annular fluid conduit. In one or more embodiments, the catalyst is coated on an interior surface of the exterior shell. In one or more embodiments, the catalyst is coated on an exterior surface of the membrane. In one or more embodiments, the catalyst is located in the interior fluid conduit. In one or more embodiments, the catalyst is coated on an interior surface of the membrane. In one or more embodiments, the catalyst is located in pores of the membrane.

An exhaust gas containing methane may be fed to one of the interior fluid conduit or the annular fluid conduit such that it may contact the catalyst. When OCM reaction is performed, air containing oxygen may be fed to the void without the catalyst and oxygen may permeate through the membrane to the void containing the catalyst for reaction.

When the SMR reaction is performed, hydrogen is produced in the chamber containing the catalyst. The hydrogen then may permeate through the membrane to the chamber without the catalyst to obtain a high purity hydrogen.

Figure 1B:
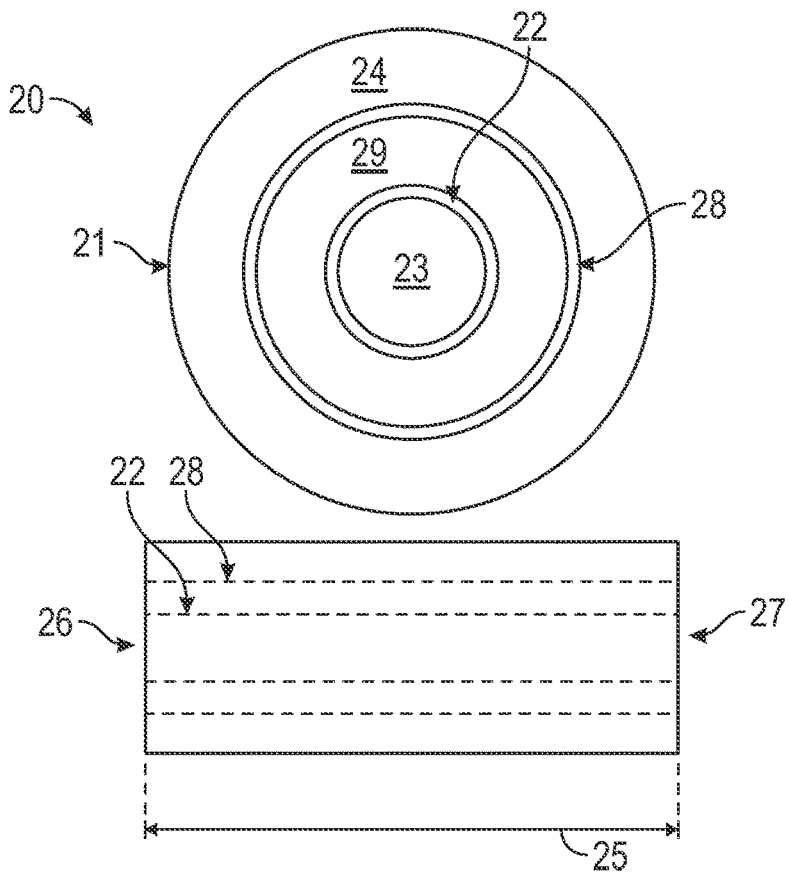
FIG. 1B is an end-view and a side view of a second membrane-based reactor according to one or more embodiments.

FIG. 1B shows an end view and a side view of a second membrane-based reactor according to one or more embodiments. Second membrane-based reactor 20 comprises a tubular exterior shell 21, a first interior shell 22, and a second interior shell 28 concentrically positioned such that the two interior shells are within the interior void formed by the exterior shell 11, and that the first interior shell 22 is positioned within the interior void formed by the second interior shell 28. Exterior shell 21 is not permeable to any of the fluids utilized in or created by membrane-based reactor 20. The concentric positioning of the interior shells 22, 28 within the tubular exterior shell 21 creates three void spaces along the length 25 (between first end 26 and second end 27) of the membrane-based reactor 20: an interior fluid conduit 23, an inner annular fluid conduit 29 and an outer annular fluid conduit 24. In one or more embodiments, a part or all of the first interior shell is formed by a first membrane. In one or more embodiments, a part or all of the second interior shell is formed by a second membrane.

In one or more embodiments, a catalyst for the OCM reaction is located in the outer annular fluid conduit. In one or more embodiments, the catalyst is coated on an interior surface of the exterior shell. In one or more embodiments, the catalyst is coated on an exterior surface of the second membrane. In one or more embodiments, the catalyst is coated on an interior surface of the second membrane. In one or more embodiments, the catalyst is located in the inner annular fluid conduit. In one or more embodiments, the catalyst is coated on an exterior surface of the first membrane. In one or more embodiments, the catalyst is located in the interior fluid conduit. In one or more embodiments, the catalyst is coated on an interior surface of the first membrane.

In one or more embodiments, a catalyst for the SMR reaction is located in the outer annular fluid conduit. In one or more embodiments, the catalyst is coated on an interior surface of the exterior shell. In one or more embodiments, the catalyst is coated on an exterior surface of the second membrane. In one or more embodiments, the catalyst is coated on an interior surface of the second membrane. In one or more embodiments, the catalyst is located in the inner annular fluid conduit. In one or more embodiments, the catalyst is coated on an exterior surface of the first membrane. In one or more embodiments, the catalyst is located in the interior fluid conduit. In one or more embodiments, the catalyst is coated on an interior surface of the first membrane.

In one or more embodiments, a dual function catalyst for both the OCM reaction and the SMR reaction is located in the outer annular fluid conduit. In one or more embodiments, the dual function catalyst is coated on an interior surface of the exterior shell. In one or more embodiments, the dual function catalyst is coated on an exterior surface of the second membrane. In one or more embodiments, the dual function catalyst is coated on an interior surface of the second membrane. In one or more embodiments, the dual function catalyst is located in the inner annular fluid conduit. In one or more embodiments, the dual function catalyst is coated on an exterior surface of the first membrane. In one or more embodiments, the dual function catalyst is located in the interior fluid conduit. In one or more embodiments, the dual function catalyst is coated on an interior surface of the first membrane.

In one or more embodiments, both a catalyst for the OCM reaction and a catalyst for the SMR reaction may be disposed in the inner annular fluid conduit 29. The two catalysts may be separated, mixed, or in series. The exhaust gas containing methane and water are directed to the inner annular fluid conduit 29 such that it contacts both catalysts.

Air containing oxygen is directed to the outer annular fluid conduit 24. Oxygen is selectively separated and permeates through the second membrane on the first interior shell 22 to the inner annular fluid conduit 29 to facilitate the OCM reaction. Ethylene may be produced in the inner annular fluid conduit 29. Hydrogen produced from the SMR reaction may selectively permeate through the first membrane on the second interior shell 28 into the interior fluid conduit 23 to obtain a high purity hydrogen.

In one or more embodiments, a dual function catalyst for the OCM reaction and the SMR reaction may be disposed in the inner annular fluid conduit 29. The exhaust gas containing methane and water are directed to the inner annular fluid conduit 29 such that it contacts the catalyst. Air containing oxygen is directed to the outer annular fluid conduit 24. Oxygen is selectively separated and permeates through the second membrane on the first interior shell 22 to the inner annular fluid conduit 29 to facilitate the OCM reaction. Ethylene may be produced in the inner annular fluid conduit 29. Hydrogen produced from the SMR reaction may selectively permeate through the first membrane on the second interior shell 28 into the interior fluid conduit 23 to obtain a high purity hydrogen.

In one or more embodiments, the catalyst for OCM reaction may be disposed in one of the annular fluid conduits and the catalyst for SMR reaction may be disposed in an adjacent annular fluid conduit. There may or may not be a membrane between the two annular fluid conduits. The heat generated from the OCM reaction may transfer to the adjacent annular fluid conduit to facilitate SMR reaction.

In one or more embodiments, the catalyst for the OCM reaction may be disposed in the inner annular fluid conduit 29 and the catalyst for the SMR reaction may be disposed in the interior annular fluid conduit 23. The exhaust gas containing methane is directed to the inner annular fluid conduit 29 such that it contacts the catalyst for the OCM reaction. The exhaust gas containing methane and water are directed to the interior annular fluid conduit 23 such that it contacts the catalyst for the SMR reaction. Air containing oxygen is directed to the outer annular fluid conduit 24. Oxygen is selectively separated and permeates through the first membrane on the first interior shell 22 to the inner annular fluid conduit 29 for the OCM reaction. Ethylene may be produced in the inner annular fluid conduit 29. Hydrogen produced from the SMR reaction selectively permeates through the second membrane on the second interior shell 28 into the interior fluid conduit 23 to obtain a high purity hydrogen.

Note that the design of the membrane-based reactor is not limited to the previously-described embodiments. The membrane-based reactor may be of any shape and configuration that fits the operation of the marine engine system.

In one or more embodiments, the catalyst for the OCM reaction may comprise a metal oxide, or a metal oxide composite, or a metal. For example, the catalyst may comprise $Fe_2O_3$, $V_2O_5$, $MoO_3$, $CO_3O_4$, Pt—Rh, $ZrO_2$, $Li/ZrO_2$, Ag—Au, $Au/CO_3O_4$, Co/Mn, $CeO_2$, MgO, $La_2O_3$, $Mn_3O_4$, $Na_2WO_4$, MnO, ZnO, $LiAlO_2$, $Cr_2O_3$, $Mn_2O$, $SnO_2$, $TiO_2$, or a combination thereof, on various supports. The catalyst may comprise dopants for improving catalytic activity (for example, Cl, Mn, W) or product selectivity (for example, Na, Cs, Sr, Ba). The support may be a refractory oxide. In one or more embodiments, the support may be $Al_2O_3$.

In one or more embodiments, the catalyst for the SMR reaction may base on Pt, Pd, Rh, Ni, or a combination thereof, on various supports. The support may be a refractory oxide. In one or more embodiments, the support may be $Al_2O_3$. The catalyst may comprise 3-30 wt % of one or more metal, based on the weight of the catalyst. In one or more embodiments, the catalyst may be a bimetal catalyst, for example, a Ni-based catalyst with 0.5-2 wt % of Pt or Pd.

In one or more embodiments, the catalyst may be a dual function catalyst capable of converting methane through both OCM and SMR reactions.

The membrane-based reactor according to one or more embodiments may include a catalyst converting methane into ethylene in a range of from about 500 to 1000° C.

The SMR reaction is endothermic. While the OCM reaction is exothermic, a high temperature is required to generate methyl free radicals and increase selectivity toward ethylene. In one or more embodiments, exhaust energy may provide energy to the reactor to support one or more reactions. Exhaust energy may be in the form of exhaust heat (waste heat) carried by the exhaust gas. In one or more embodiments, the exhaust heat is carried by a portion of the exhaust gas directed into the membrane-based reactor to provide energy to the reaction. In one or more embodiments, the exhaust heat is carried by a portion of the exhaust gas directed to exterior of the membrane-based reactor to provide energy to the reaction. In one or more embodiments, a temperature control device may be used to control a temperature of the catalytic reactor, for example, to provide heat or cooling, to either raise or reduce the temperature to a desired degree to induce reaction.

Figure 2:
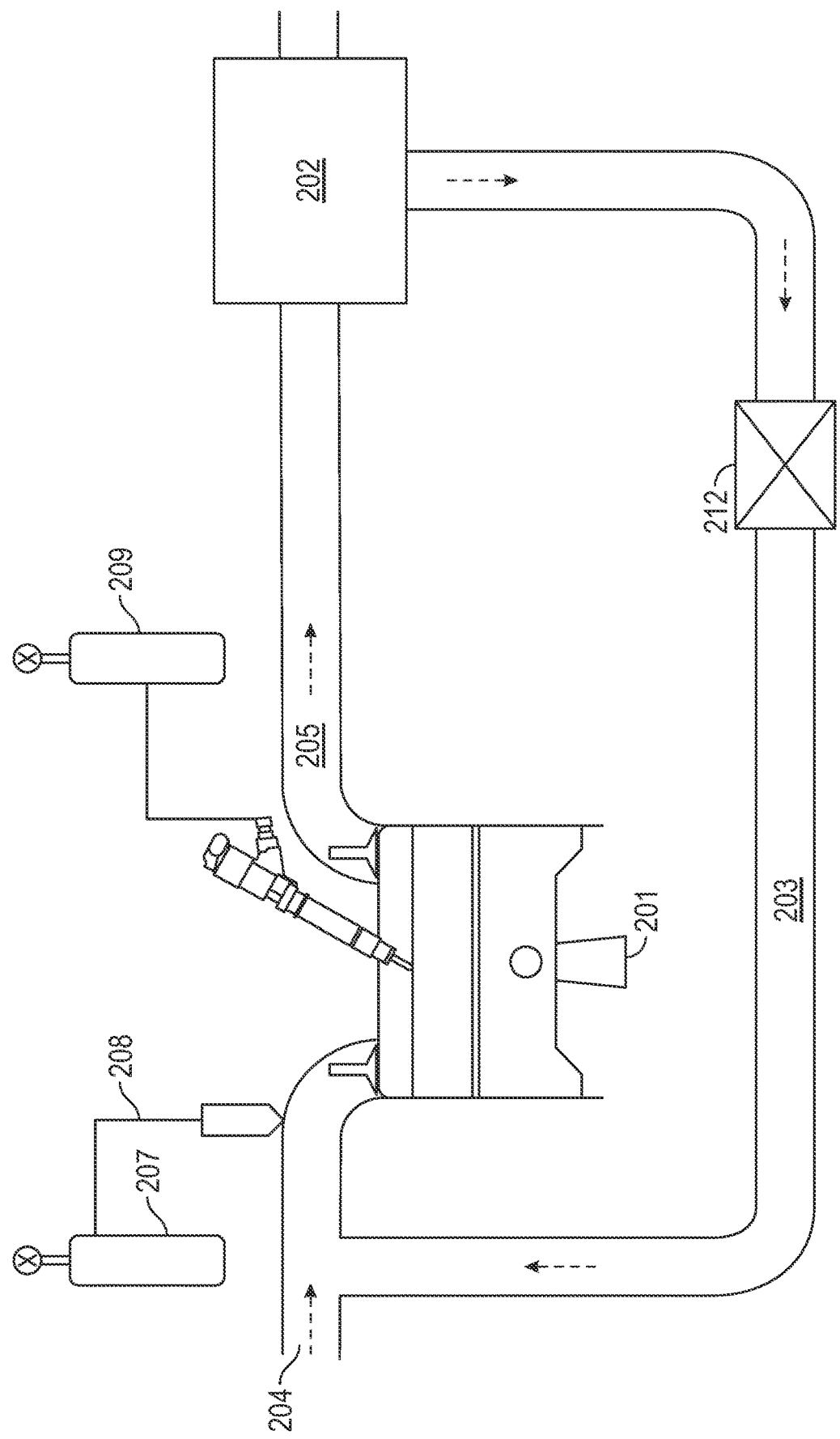
FIG. 2 shows a marine engine system according to one or more embodiments comprising a reactor for oxidative coupling of methane.

According to one or more embodiments, the marine engine system may comprise an engine and a catalytic reactor for conducting an OCM reaction. FIG. 2 shows a marine engine system according to one or more embodiments comprising a reactor for OCM reaction. LNG from an LNG tank 207 is introduced as fuel into the engine 201 through a fuel injector 208. The fuel injector 208 is a port fuel injection (PFI) injector. The LNG is mixed with air from an air inlet 204. Diesel from a diesel tank 209 may be introduced as a pilot igniter for a lean air-fuel mixture. An exhaust gas 205 containing methane is directed to the catalytic reactor 202 for OCM reaction. In one or more embodiments, a temperature control device may be used to control a temperature of the catalytic reactor, for example, to provide heat or cooling, to either raise or reduce the temperature to a desired degree to induce reaction. $C_2$ hydrocarbons (that is, ethylene and ethane) are formed on the surface of a catalyst within the catalytic reactor 202 as previously described. One or more gases may be recirculated back to the engine, through a recirculation loop 203, to improve combustion rate, increase engine efficiency, and reduce emissions, as described previously. In one or more embodiments, ethylene, as a product of the OCM reaction, is recirculated back to the engine, through the recirculation loop 203. In one or more embodiments, one or more of unreacted methane, ethylene, carbon monoxide, and other species from the OCM reaction may be recirculated back the recirculation loop 203. In one or more embodiments, the recirculation loop recirculates to an intake of the engine. In one or more embodiments, the recirculation loop may be an EGR loop. Optionally, carbon dioxide, water, or both may be removed from the products of the reaction through a treatment device 212 coupled to the recirculation loop, as described previously. After removal of carbon dioxide, water, or both, the remaining retentate components (for example, carbon monoxide, $C_2$ hydrocarbon, unreacted methane, air) from the reaction may be recirculated back to the engine.

Figure 3:
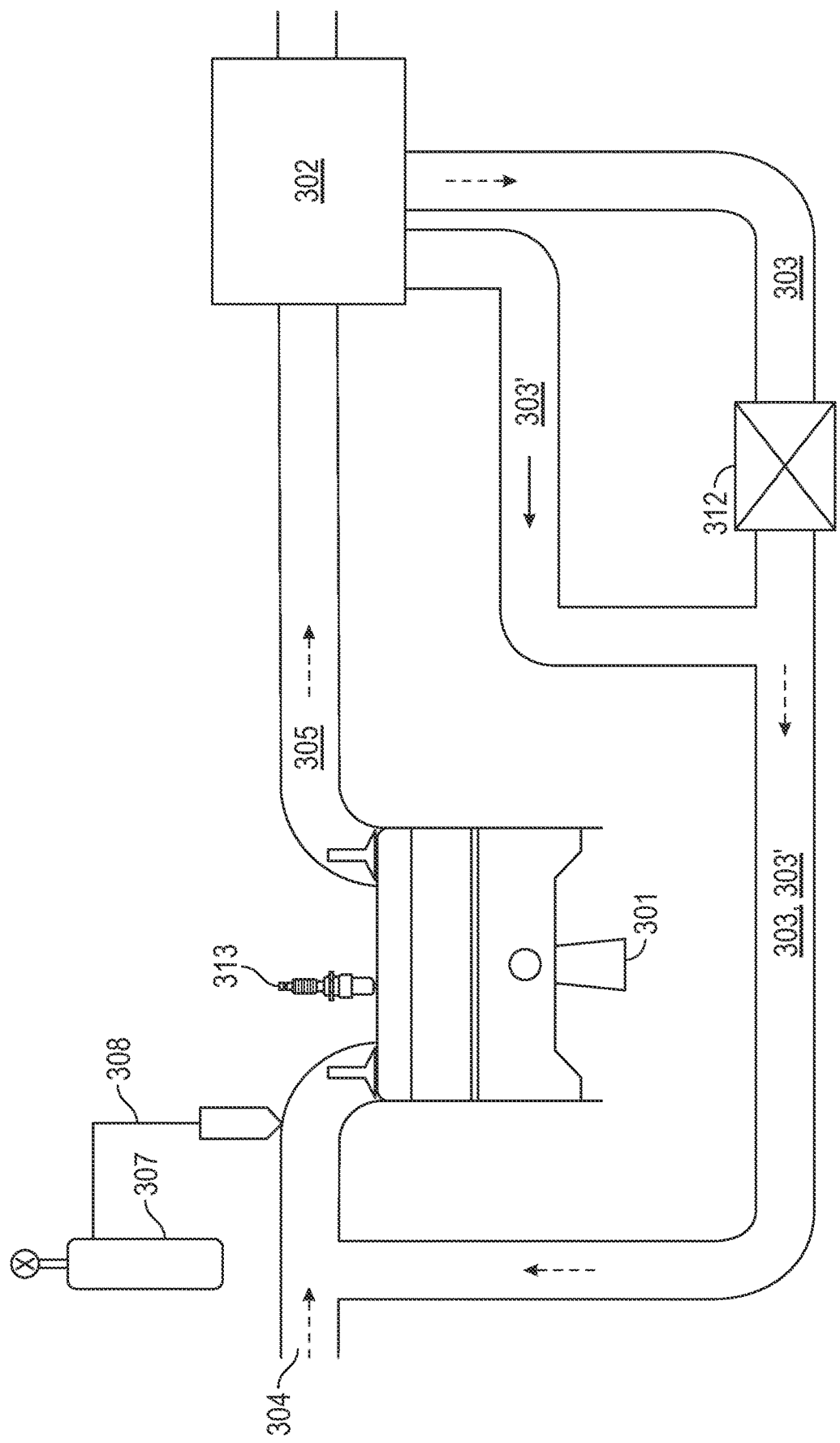
FIG. 3 shows a marine engine system according to one or more embodiments.

According to one or more embodiments, the marine engine system may comprise a spark ignited engine and a catalytic reactor for a SMR reaction. FIG. 3 shows a marine engine system according to one or more embodiments comprising a reactor for SMR reaction. LNG from an LNG tank 307 is introduced as fuel into to the engine 301 through a fuel injector 308. In one or more embodiments, the spark ignited engine is a lean burn spark ignited engine. In one or more embodiments, the spark ignited engine is a stoichiometric spark ignited engine. The fuel injector 208 is a pot fuel injection (PFI) injector. The LNG is mixed with air from an air inlet 304. A spark plug 313 is used to ignite the air-fuel mixture. An exhaust gas 305 containing methane is directed to the catalytic reactor 302 for SMR reaction. In one or more embodiments, a temperature control device may be used to control a temperature of the catalytic reactor. One or more gases may be recirculated back to the engine, through one or more of recirculation loops 303 and 303', to improve combustion rate, increase engine efficiency, and reduce emissions, as described previously. Hydrogen and carbon monoxide (syngas) are formed on the surface of a catalyst of the catalytic reactor 302, as previously described. In one or more embodiments, high purity hydrogen is recirculated back to the engine, through the recirculation loop 303'. In one or more embodiments, one or more of hydrogen, carbon monoxide, and unreacted methane may be recirculated back to the engine, through the recirculation loop 303. In one or more embodiments, the recirculation loop recirculates to an intake of the engine. In one or more embodiments, the recirculation loop may be an EGR loop. Optionally, carbon dioxide, water, or both may be removed from the products of the reaction through a treatment device 312 coupled to the recirculation loop, as described previously. After removal of carbon dioxide, water, or both, the remaining retentate components (for example, carbon monoxide, $C_2$ hydrocarbon, unreacted methane, air) from the reaction may be recirculated back to the engine through the recirculation loop 303, optionally combined with high purity hydrogen in the recirculation loop 303'.

Figure 4:
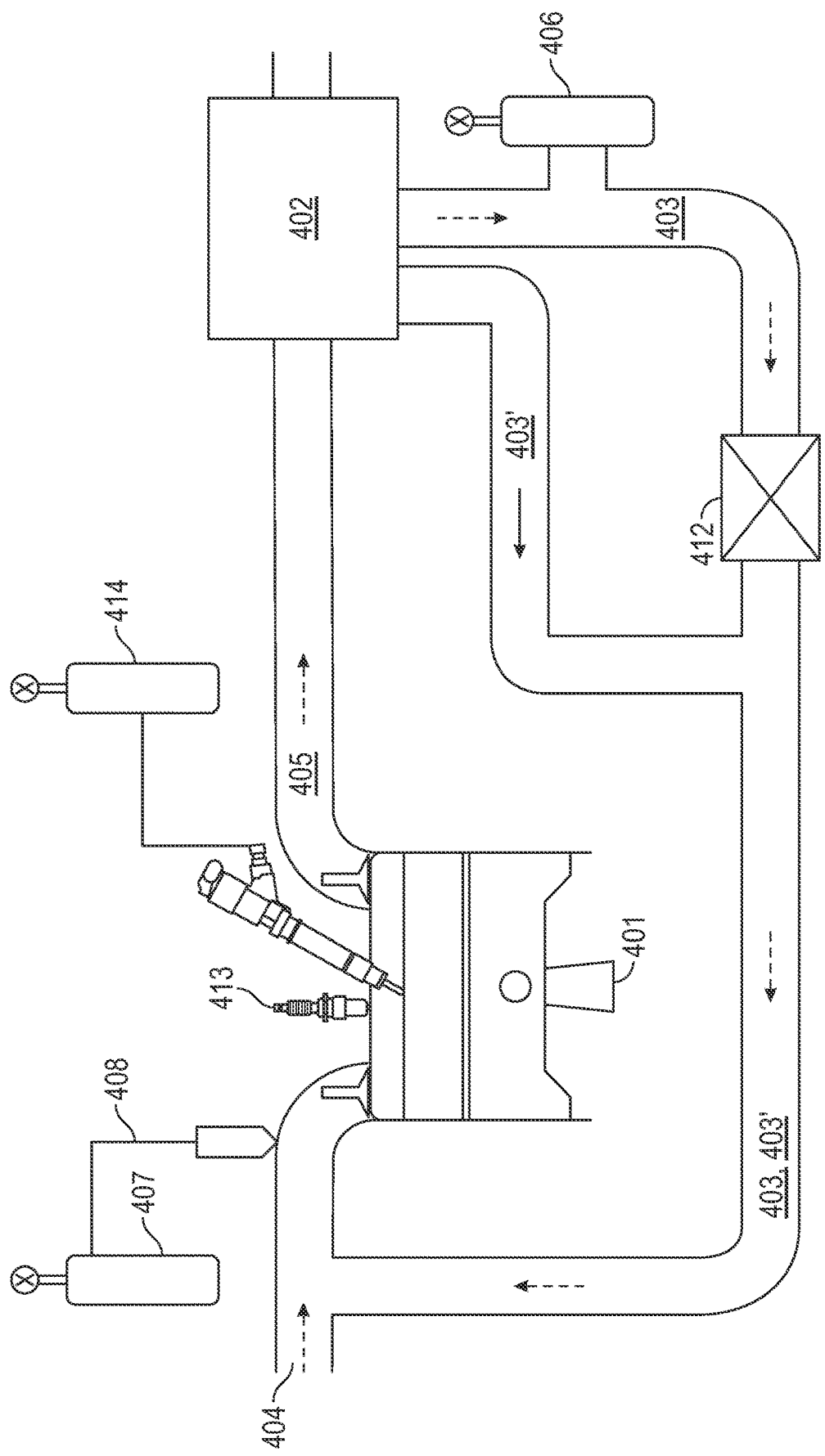
FIG. 4 shows a marine engine system according to one or more embodiments comprising a water injector.

The increased flame speed through hydrogen recirculation may also help to reduce engine knocking. Marine engines are large bore engines with a high compression ratio compared to other light duty engines (for example, an automotive engine). This may lead to engine knocking during spark ignition operation, especially at high load conditions. In one or more embodiments, the marine engine system may comprise a water injector to minimize engine knocking. FIG. 4 shows a marine engine system according to one or more embodiments comprising a water injector. LNG from an LNG tank 407 is introduced as fuel into the engine 401 through a fuel injector 408. Fuel injector is a port fuel injection (PFI) injector. The LNG is mixed with air from an air inlet 404. A spark plug 413 is used to ignite the air-fuel mixture. An exhaust gas 405 containing methane is directed to the catalytic reactor 402 for SMR reaction, where hydrogen and carbon monoxide are formed on the surface of a catalyst within the catalytic reactor 402, as previously described. In one or more embodiments, a temperature control device may be used to control a temperature of the catalytic reactor. In one or more embodiments, products ($H_2$ and CO) of the SMR reaction may be separately stored in a syngas tank 406. One or more gases may be recirculated back to the engine, through one or more recirculation loop 403 and 403', to improve combustion rate, increase engine efficiency, and reduce emissions, as described previously. In one or more embodiments, high purity hydrogen may be recirculated back to the engine through the recirculation loop 403'. In one or more embodiments, one or more of hydrogen, carbon monoxide, and unreacted methane may be recirculated back to the engine through the recirculation loop 403. In one or more embodiments, the recirculation loop recirculates to an intake of the engine. In one or more embodiments, the recirculation loop may be an EGR loop. Optionally, carbon dioxide, water, or both may be removed from the products of the reaction through a treatment device 412 coupled to the recirculation loop, as described previously. After removal of carbon dioxide, water, or both, all remaining retentate components (for example, carbon monoxide, $C_2$ hydrocarbon, unreacted methane, air) from the reaction may be recirculated back to the engine through the recirculation loop 403, optionally combined with high purity hydrogen in the recirculation loop 403'.

In one or more embodiments, the water injector 414 may spray water into the intake manifold or directly into combustion chambers of the engine. Due to the latent heat of vaporization, ignition delay may be prolonged and combustion rate may be slowed down in the engine, thus reduce engine shock at high load. In addition, the exhaust gas may carry the water molecules to the catalytic reactor such that water is not separately supplied for the SMR reaction.

In one or more embodiments, when the engine operates at high load condition, the products ($H_2$ and CO) of the SMR reaction are stored separately in a syngas tank 406. The stored gases may be supplied back to the engine when operating at low loads.

Figure 5:
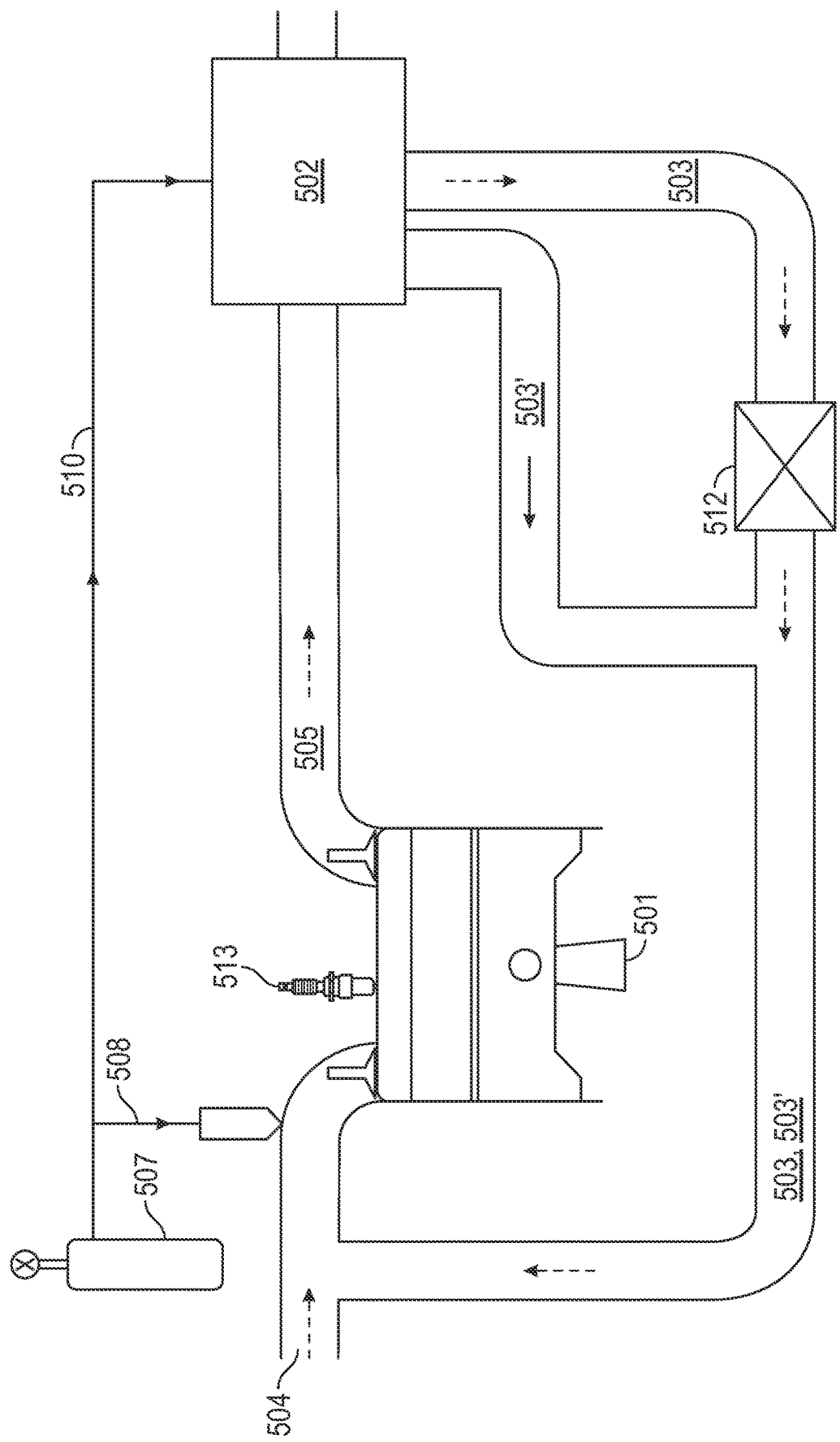
FIG. 5 shows a marine engine system according to one or more embodiments comprising a reactor for oxidative coupling of methane and steam methane reforming.

The marine engine system according to one or more embodiments may comprise an engine and a catalytic reactor for combined OCM and SMR reactions. FIG. 5 shows a marine engine system according to one or more embodiments comprising a reactor for both OCM and SMR reactions. LNG from an LNG tank 507 is introduced as fuel into the engine 501 through a fuel injector 508. Injector 508 is a pot fuel injection (PFI) injector. The LNG is mixed with air from an air inlet 504. The marine engine system may operate in compression ignition or spark ignition modes. A spark plug 513 may be used to ignite the air-fuel mixture. An exhaust gas 505 containing methane is directed to the catalytic reactor 502 for both an OCM and a SMR reaction. The methane in the exhaust gas may undergo one or both reactions. The conversion of methane and production of desired products may be increased. In one or more embodiments, a dual function catalyst may be used to catalyze both OCM and SMR reactions and to maximize conversion of methane. Because the OCM reaction is exothermic and the SMR reaction is endothermic, heat generated from the exothermic reaction may facilitate and activate the catalyst for the SMR reaction. In one or more embodiments, a temperature control device may be used to control a temperature of the catalytic reactor.

One or more gases may be recirculated back to the engine, through one or more recirculation loop 503 and 503', to improve ignition, combustion, and knocking characteristics of the engine under different modes of combustion. In one or more embodiments, high purity hydrogen may be recirculated back to the engine through a recirculation loop 503'. In one or more embodiments, one or more of the reaction products (for example, $C_2$ hydrocarbons, hydrogen, and CO) may be recirculated back into the engine through the recirculation loop 503. In one or more embodiments, the recirculation loop recirculates to an intake of the engine. In one or more embodiments, the recirculation loop may be an EGR loop. Optionally, carbon dioxide, water, or both may be removed from the products of the reaction through a treatment device 512 coupled to the recirculation loop, as described previously. After removal of carbon dioxide, water, or both, all remaining retentate components (for example, carbon monoxide, $C_2$ hydrocarbon, unreacted methane, air) from the reaction may be recirculated back to the engine through the recirculation loop 503, optionally combined with high purity hydrogen in the recirculation loop 503'.

In one or more embodiments, methane converted in the catalytic reactor is supplied by both the exhaust gas and fresh feed from the LNG tank. As shown in FIG. 5, additional feed 510 from the LNG tank 507 may be supplied under lean condition to meet the efficiency target. In particular, at low load condition, there may be a greater demand for the reaction products. Based on the requirements at different load or speed conditions, the additional direct feed from LNG tank 507 to catalytic reactor 502 through line 510 may be utilized. The EGR levels and fuel flow to the reactor will be regulated to obtain the required fuel-to-air equivalence ratio at the catalyst surface in the catalytic reactor 502.

The marine engine system according to one or more embodiments may further contain one or more controller and one or more sensor for controlling engine operation and acquiring engine operating parameters. The controller may be in signal communication with the sensor such that the flow of the recirculation loop cooperates with the fuel injector to the intake manifold. Based on operating loads or conditions (for example, low, normal, cold start, and high), the controller may regulate the reaction products to optimize the efficiency of the engine. A programmable logic controller (PLC) may be used to control the flow of recirculated products into the engine. Optionally, one of more of pressure regulator or let down device, flow control valve, storage tank, and venting valve may be used.

The marine engine system according to one or more embodiments may comprise a feed that is introduced to the engine, including LNG and the reaction product from at least one of the OCM and SMR reaction. The feed may include at least 1% of the reaction product, or at least 10% of the reaction product, or at least 20% of the reaction product, or at least 30% of the reaction product, by volume of the total feed to the engine.

According to one or more embodiments, the marine engine system may be applied on-board to medium speed engines used in ships for propulsion or power generation. Comparing to automotive engines, an exhaust temperature from the marine engine may be higher, which is sufficient to active a catalytic reaction.

The marine engine system of the present disclosure may provide one or more advantages. Overall methane reduction is realized by both improved combustion rate inside the engine and catalytic reactions for methane conversion. The recirculation of ethylene may facilitate low temperature combustion and improve stability in a dual fuel compression ignition engine fueled by lean burn LNG. When the engine operates in low load and lean burn conditions, the temperature in the engine is lower, resulting in incomplete combustion (more unburnt methane). Further, a cycle-to-cycle combustion stability is poor in low load condition. Ethylene may shorten ignition delay and combustion duration, providing a high reactivity and improvement in combustion stability. Because the recirculation of ethylene enables operation under low temperature, emissions of hydrocarbons, nitrogen oxides, carbon monoxide, and soot emissions may be reduced. A lean limit may be extended, improving the indicated thermal efficiency of the engine. The recirculating of hydrogen may increase flame speed and reduce combustion rate. Further, the recirculation of hydrogen extends a dilution tolerance of exhaust gas recirculation (EGR) in stoichiometric spark ignited engine. Stoichiometric spark ignited engine fueled by LNG suffer from lower break thermal efficiency. While dilution by EGR may provide reduced pumping work, which enables wide-open throttle operation at part load condition, it is limited due to cycle-to-cycle combustion stability. The recirculation of hydrogen may improve the combustion stability, therefore extend the dilution tolerance and increase the efficiency.

Prophetic Examples

The following examples are merely illustrative and should not be interpreted as limiting the scope of the present disclosure.

Example 1

In one or more embodiments, unburnt methane in the exhaust gas may be converted to desired products in the catalytic reactor through an OCM reaction. OCM product from the reaction is recirculated back to the engine. The OCM product contains mainly ethylene with certain amount of carbon monoxide and carbon dioxide as byproducts from side reaction (a syngas producing reaction). Modelling on a homogenous batch reactor (0-D) at 35 bar and 850 K intake conditions was performed to demonstrate that existence of OCM product has significant effect on fuel reactivity.

Figure 6A:
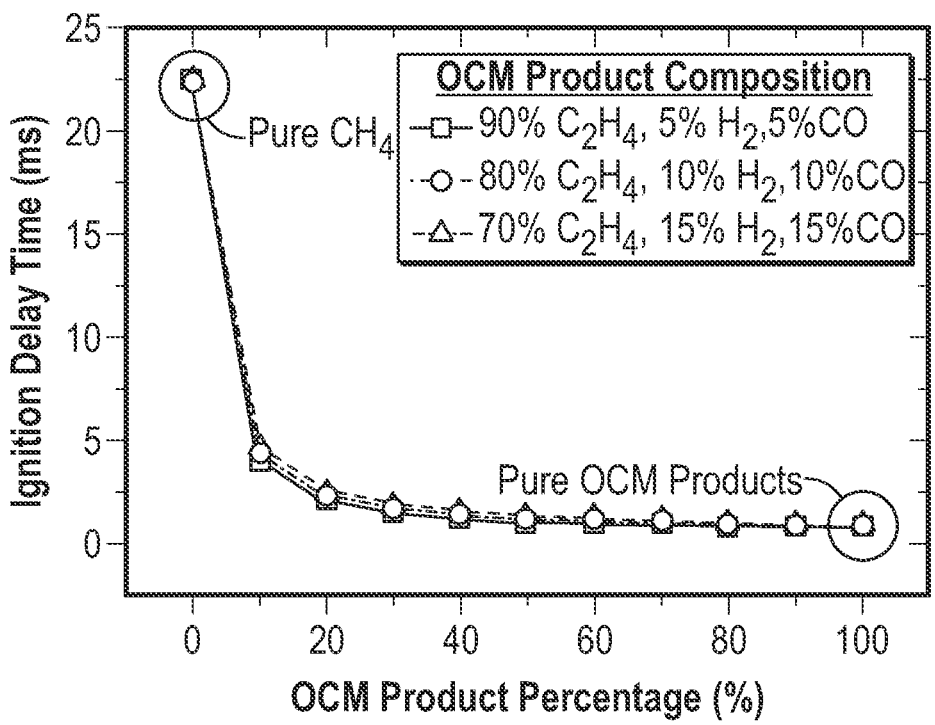
FIG. 6A shows modelling results of ignition delay time in a marine engine system according to one or more embodiments.

FIG. 6A shows ignition delay time of the engine when the recirculated gas contains different percentage of ethylene, hydrogen, and carbon monoxide. The OCM product may contain 90% of ethylene, 5% of hydrogen, and 5% of carbon monoxide; or 80% of ethylene, 10% of hydrogen, and 10% of carbon monoxide; or 70% of ethylene, 15% of hydrogen, and 15% of carbon monoxide.

The combustion phasing and indicated thermal efficiency of a homogeneous charge compression ignition (HCCI) engine (1-D) was modeled using CHEMKIN® software (Ansys, Inc. Corp.; Delaware, USA). The model used a compression ignition engine configuration with a compression ratio of 18. When no recirculation of OCM product is performed (pure methane as fuel), a longer ignition delay time was observed. The ignition delay time significantly decreased even when a percentage of OCM product is merely 10%. As the percentage of OCM product increases, the ignition delay time kept decreasing under all ethylene concentrations.

Figure 6B:
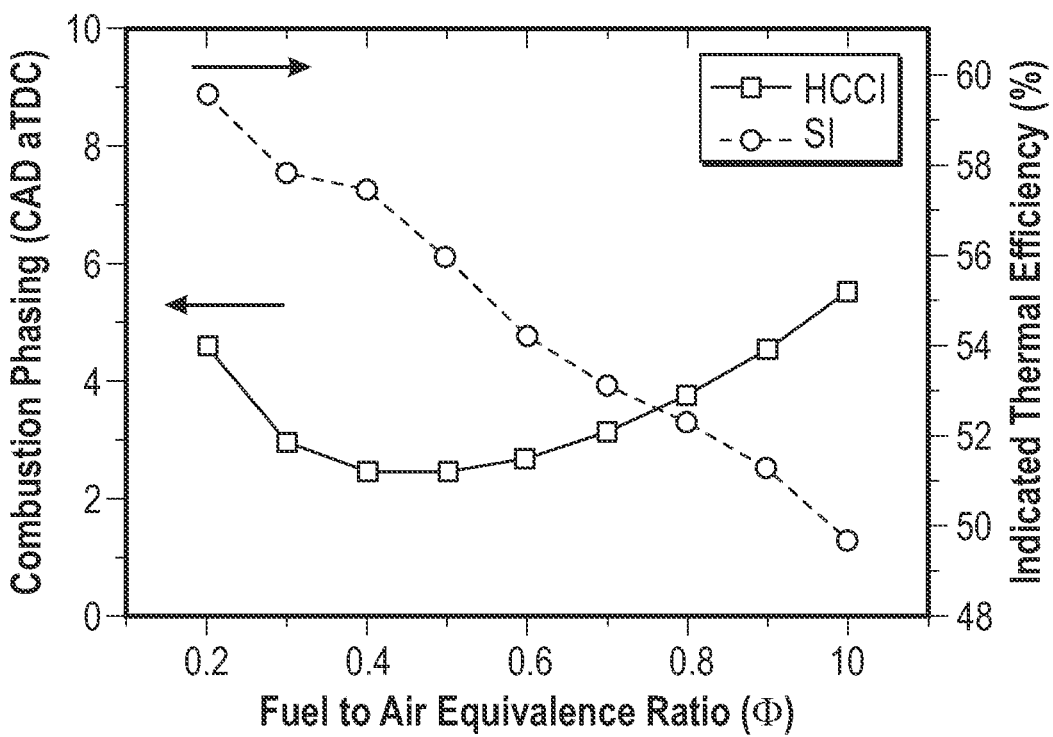
FIG. 6B shows modelling results of combustion phasing and indicated thermal efficiency in a marine engine system according to one or more embodiments.

FIG. 6B shows the modelling of combustion phasing and indicated thermal efficiency of a HCCI engine with a compression ratio of 18. The fuel feed comprises 80% of LNG and 20% of OCM product. The OCM product includes 90% of ethylene, 5% of carbon monoxide, and 5% of hydrogen. A minimum of 20% of OCM product is required to achieve a desired efficiency improvement. Comparing to a spark ignition (SI) engine with a compression ratio of 12 and an indicated thermal efficiency of 52.5%, the modelling results demonstrated that there may be up to about a 10% improvement in indicated thermal efficiency when the lean limit is less than an equivalence ratio of 0.6. The lean limit was extended up to a fuel-to-air equivalence ratio of 0.3 for HCCI engine fueled by LNG with improved efficiency.

Example 2

In one or more embodiments, SMR reaction is performed to convert methane in the exhaust gas into syngas ($H_2$ and CO). Hydrogen may be recirculated back to a spark ignited engine to increase flame speed. Hydrogen may also extend the lean limit of the air-fuel mixture so as to increase the engine efficiency.

Figure 7:
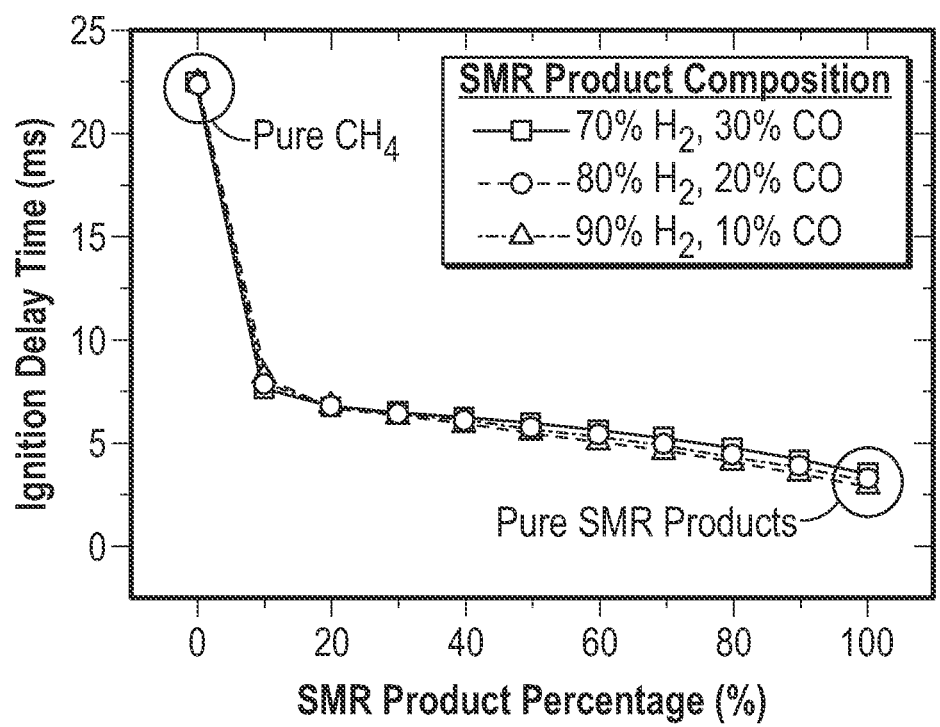
FIG. 7 shows modelling results of ignition delay time in a marine engine system according to one or more embodiments.

FIG. 7 shows modelling results of ignition delay time in a homogenous batch reactor (0-D) at 35 bar and 1000 K intake conditions when the recirculated gas contains product from the SMR reaction. The product from the SMR reaction may contain 70% of hydrogen and 30% of carbon monoxide, or 80% of hydrogen and 20% of carbon monoxide, or 90% of hydrogen and 10% of carbon monoxide. When no recirculation of SRM product is performed (pure methane as fuel), a longer ignition delay time was observed. The ignition delay time significantly decreased even when a percentage of SMR product is merely 10%. As a percentage of SMR product increases, an immediate decrease in ignition delay time was observed, and the ignition delay time kept decreasing with increased percentage of SMR product. The modelling results show that reformed hydrogen and carbon monoxide help to reduce the knock intensity and the operation under higher compression ratio offers increased efficiency.

Unless defined otherwise, all technical and scientific terms used have the same meaning as commonly understood by one of ordinary skill in the art to which these systems, apparatuses, methods, processes, and compositions belong.

As used here and in the appended claims, the words "comprise," "has," and "include" and all grammatical variations thereof are each intended to have an open, non-limiting meaning that does not exclude additional elements or steps.

When the words "approximately" or "about" are used, this term may mean that there can be a variance in value of up to ±10%, of up to 5%, of up to 2%, of up to 1%, of up to 0.5%, of up to 0.1%, or up to 0.01%.

Ranges may be expressed as from about one particular value to about another particular value, inclusive. When such a range is expressed, it is to be understood that another embodiment is from the one particular value to the other particular value, along with all particular values and combinations thereof within the range.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, any means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112(f) for any limitations of any of the claims, except for those in which the claim expressly uses the words 'means for' together with an associated function.

What is claimed:

1. An engine system comprising:
   an engine configured to combust liquid natural gas and generate an exhaust gas comprising methane;
   a catalytic reactor coupled downstream of the engine and configured to convert methane into a product through one or more of oxidative coupling of methane (OCM) reaction and steam methane reforming (SMR) reaction; and
   a recirculation loop configured to recirculate at least a part of the product back to the engine, wherein the catalytic reactor is configured to convert methane into ethylene through the OCM reaction;
   the catalytic reactor further comprises an oxygen permeable membrane to supply oxygen to the catalytic reactor; and
   the recirculation loop is configured to recirculate the ethylene in the product to the engine to increase combustion efficiency.

2. The engine system of claim 1, further comprising a treatment device coupled to the recirculation loop configured to remove carbon dioxide, water, or both, from the product; and
   wherein the recirculation loop is configured to recirculate the product to the engine after removal of carbon dioxide, water, or both.

3. The engine system of claim 1, wherein:
   the catalytic reactor is configured to convert methane through the SMR reaction;
   the catalytic reactor further comprises a hydrogen permeable membrane; and
   the recirculation loop is configured to recirculate hydrogen that permeates through the hydrogen permeable membrane to the engine.

4. The engine system of claim 1, further comprising a treatment device coupled to the recirculation loop configured to remove carbon dioxide, water, or both from the product;
   wherein the catalytic reactor is configured to convert methane through the SMR reaction; and
   wherein the recirculation loop is configured to recirculate the product to the engine after removal of carbon dioxide, water, or both.

5. The engine system of claim 1, wherein:
   the catalytic reactor is configured to convert methane through the OCM reaction and the SMR reaction;
   the catalytic reactor further comprises a hydrogen permeable membrane; and
   the recirculation loop is configured to recirculate hydrogen that permeates through the hydrogen permeable membrane to the engine.

6. The engine system of claim 1, further comprising a treatment device coupled to the recirculation loop configured to remove carbon dioxide, water, or both, from the product;
   wherein the catalytic reactor is configured to convert methane through the OCM reaction and the SMR reaction; and
   wherein the recirculation loop is configured to recirculate the product to the engine after removal of carbon dioxide, water, or both.

7. The engine system of claim 1, wherein the engine type is selected from the group consisting of a dual fuel compression ignition engine and a spark ignited engine.

8. The engine system of claim 1, further comprising a temperature control device that is configured to control a temperature of the catalytic reactor.

9. The engine system of claim 1, wherein the catalytic reactor is configured to utilize exhaust energy carried by the exhaust gas for at least one of the OCM reaction and SMR reactions.

10. The engine system of claim 1, further comprising a water injector that is configured to introduce water into the engine.

11. A vessel comprising the engine system of claim 1.

12. A method comprising:
    operating an engine system such that:
    a fuel comprising liquid natural gas is introduced into an engine, an exhaust gas comprising methane is directed from the engine to a catalytic reactor, methane is converted to a product through one or more of oxidative coupling of methane (OCM) reaction and steam methane reforming (SMR) reactions, and at least a part of the product is recirculated to the engine, wherein oxygen is supplied to the catalytic reactor through an oxygen permeable membrane;

methane is converted to ethylene through the OCM reaction in the catalytic reactor, and the ethylene in the product is recirculated to the engine to increase combustion efficiency.

13. The method of claim 12, further comprising operating the engine system such that carbon dioxide, water, or both, are removed from the product;

wherein the product is recirculated to the engine after removing carbon dioxide, water, or both.

14. The method of claim 12, further comprising operating the engine system such that hydrogen is obtained from the product using a hydrogen permeable membrane;

wherein methane is converted to the product through the SMR reaction, and wherein hydrogen that permeates the hydrogen permeable membrane is recirculated to the engine.

15. The method of claim 12, further comprising operating the engine system such that carbon dioxide, water, or both, is removed from the product;

wherein methane is converted to the product through the SMR reaction; and wherein the product is recirculated to the engine after the removing carbon dioxide, water, or both.

16. The method of claim 12, further comprising operating the engine system such that hydrogen is obtained from the product using a hydrogen permeable membrane;

wherein methane is converted to the product through the OCM and the SMR reactions, and wherein hydrogen that permeates the hydrogen permeable membrane is recirculated to the engine.

17. The method of claim 12, further comprising operating the engine system such that carbon dioxide, water, or both, is removed from the product;

wherein methane is converted to the product through the OCM and the SMR reactions;

wherein the product is recirculated to the engine after the removing carbon dioxide, water, or both.

18. The method of claim 12, further comprising operating the engine system such that a temperature of a catalytic reactor is controlled utilizing a temperature control system.

19. The method of claim 12, further comprising operating the engine system such that water is introduced into the engine utilizing a water injector.

\* \* \* \* \*